(12) United States Patent
Shenfarber et al.

(10) Patent No.: US 11,752,358 B2
(45) Date of Patent: *Sep. 12, 2023

(54) DISPOSABLE PRODUCT CAP AND ASSEMBLY HAVING A MANUALLY USABLE THERMO-OPTICAL DEVICE FOR SKIN CARE

(71) Applicant: OMM Imports, Inc., Doral, FL (US)

(72) Inventors: Moti Shenfarber, Doral, FL (US); Gennadiy Berinsky, Modein (IL)

(73) Assignee: OMM Imports Inc., Doral, FL (US)

( * ) Notice: Subject to any disclaimer, the term of this patent is extended or adjusted under 35 U.S.C. 154(b) by 163 days.

This patent is subject to a terminal disclaimer.

(21) Appl. No.: 17/404,352

(22) Filed: Aug. 17, 2021

(65) Prior Publication Data

US 2022/0032082 A1 Feb. 3, 2022

Related U.S. Application Data

(63) Continuation of application No. 15/980,336, filed on May 15, 2018, now Pat. No. 11,090,506.

(51) Int. Cl.
*A61N 5/06* (2006.01)
*A61K 8/9789* (2017.01)
(Continued)

(52) U.S. Cl.
CPC ........... *A61N 5/0616* (2013.01); *A45D 34/04* (2013.01); *A45D 40/00* (2013.01); *A61K 8/922* (2013.01); *A61K 8/9789* (2017.08); *A61N 5/062* (2013.01); *A61N 5/0625* (2013.01); *A61Q 19/00* (2013.01); *A45D 2034/005* (2013.01); *A45D 2040/0012* (2013.01); *A45D 2200/05* (2013.01); *A45D 2200/155* (2013.01); *A45D 2200/205* (2013.01);
(Continued)

(58) Field of Classification Search
CPC .... A61N 5/0616; A61N 5/062; A61N 5/0625; A61K 8/9789; A61K 8/922; A45D 34/04; A45D 40/00; A45D 2034/005; A45D 2040/0012; A45D 2200/05
See application file for complete search history.

(56) References Cited

U.S. PATENT DOCUMENTS 2,853,728 A * 9/1958 Nadai ................... B65D 47/42
401/207
4,427,001 A * 1/1984 Kiefer ................ A61H 15/0092
601/19
(Continued)

FOREIGN PATENT DOCUMENTS

DE 4427001 A1 * 12/1994 ........... G01T 1/1642
FR 2853728 A3 * 10/2004 ........... G01N 27/043
WO WO-9808646 A1 * 3/1998 ............... B21H 1/04

*Primary Examiner* — Nicholas D Lucchesi
(74) *Attorney, Agent, or Firm* — The Concept Law Group, PA; Scott D. Smiley; Scott M. Garrett

(57) ABSTRACT

A cap to be placed on a head of a device for treating the skin of a user includes an inner part to be removably attached to the head of the device, an outer part to be placed against the skin of the user and an interior disposed between the inner and outer parts. A product is disposed in the interior for application to the skin of the user and a covering, such as a membrane which is disposed on the outer part or a sterilized pack, is removable before use. An assembly having the device and the cap is also provided.

17 Claims, 8 Drawing Sheets

(51) Int. Cl.
*A61K 8/92* (2006.01)
*A45D 40/00* (2006.01)
*A45D 34/04* (2006.01)
*A61Q 19/00* (2006.01)
*A45D 34/00* (2006.01)

(52) U.S. Cl.
CPC ...... *A45D 2200/25* (2013.01); *A61K 2800/81* (2013.01); *A61N 2005/063* (2013.01); *A61N 2005/0644* (2013.01); *A61N 2005/0652* (2013.01)

(56) References Cited

U.S. PATENT DOCUMENTS

| | | | | |
|---|---|---|---|---|
| 4,739,778 | A * | 4/1988 | Christie | A45D 40/0087 206/467 |
| 5,042,690 | A * | 8/1991 | O'Meara | A45D 34/042 401/207 |
| 7,204,846 | B2 * | 4/2007 | Suzuki | A61N 1/44 606/41 |
| 8,321,008 | B2 * | 11/2012 | Petersen | A61N 1/30 604/20 |
| 9,808,646 | B2 * | 11/2017 | Piergallini | A61P 17/02 |
| 9,872,813 | B2 * | 1/2018 | Giraud | A61H 15/02 |
| 2002/0055702 | A1 * | 5/2002 | Atala | A61M 37/0092 600/38 |
| 2003/0083618 | A1 * | 5/2003 | Angel | A61M 5/14248 604/141 |
| 2003/0120185 | A1 * | 6/2003 | Dirks | A61H 15/02 601/19 |
| 2003/0123919 | A1 * | 7/2003 | Gueret | A45D 34/00 401/126 |
| 2006/0058714 | A1 * | 3/2006 | Rhoades | A46B 5/0016 601/72 |
| 2007/0019004 | A1 * | 1/2007 | Ghislain Bossut | G06T 11/60 345/648 |
| 2007/0032843 | A1 * | 2/2007 | Hsu | A61N 5/06 607/88 |
| 2009/0260567 | A1 * | 10/2009 | Ozuna | A61M 37/0076 118/600 |
| 2010/0274162 | A1 * | 10/2010 | Evans | A61H 15/0092 601/46 |
| 2013/0158547 | A1 * | 6/2013 | David | A61N 5/0616 606/41 |
| 2014/0021654 | A1 * | 1/2014 | Martins | A45D 40/00 264/400 |
| 2014/0135798 | A1 * | 5/2014 | David | A61N 5/0624 606/131 |
| 2014/0219701 | A1 * | 8/2014 | Eberlein | A45D 34/041 401/2 |
| 2014/0330289 | A1 * | 11/2014 | Revivo | A46B 13/02 606/131 |
| 2014/0376984 | A1 * | 12/2014 | Villarreal | A45D 34/04 401/265 |
| 2016/0038402 | A1 * | 2/2016 | Lahousse | A61K 8/345 401/196 |
| 2017/0312490 | A1 * | 11/2017 | Unger | A61K 39/12 |
| 2018/0027950 | A1 * | 2/2018 | Choi | G01F 13/00 |
| 2019/0200726 | A1 * | 7/2019 | Shinoda | A45D 44/00 |
| 2019/0335877 | A1 * | 11/2019 | Lee | A45D 34/04 |
| 2020/0093945 | A1 * | 3/2020 | Jeong | A61N 5/0625 |

\* cited by examiner

DISPOSABLE PRODUCT CAP AND ASSEMBLY HAVING A MANUALLY USABLE THERMO-OPTICAL DEVICE FOR SKIN CARE

CROSS-REFERENCE TO RELATED APPLICATION

This application is a continuation of U.S. patent application Ser. No. 15/980,336, filed May 15, 2018, issued Aug. 17, 2021 as U.S. Pat. No. 11,090,506, the entirety of which is incorporated by reference.

FIELD OF THE INVENTION

The invention relates to a disposable product cap or capsule for manually usable thermo-optical devices for applying products, such as creams or lotions, to the skin. The invention also relates to an assembly having the device and the cap.

BACKGROUND OF THE INVENTION

There is a wide range of instruments for home use and cosmetology institutes which are constructed to treat the skin with light, heat, ultrasound and a combination thereof.

In some cases, before or after treatment, substances are applied manually for various purposes, such as increasing the effectiveness of the treatment, calming the skin from the treatment of lye, disinfecting and improving the treatment experience, etc.

Handheld devices having LEDs are known for using light therapy to treat wrinkles and discoloration of the skin. Such devices may emit invisible infrared rays that penetrate below the surface of the skin, promote collagen, reduce wrinkles and fine lines and restore elasticity.

U.S. Patent Application Publication 2014/0219701 A1 discloses a temperature modulating device 100 having a temperature modulating device element 106, a built-in applicator 102 for a fluid and a protective cap 112 to be applied when not in use.

U.S. Patent Application Publication 2010/0274162 A1 shows a massager 10 with a massage head 48, a fluid reservoir 44 and a temperature band 46 for heating and cooling a massage roller ball 42.

U.S. Patent Application Publication 2007/019004 A1 teaches a photocosmetic device with attachments 810, 820, such as a pad, for distributing lotion, etc., such as in FIG. 32 and paragraph 0187.

U.S. Patent Application Publication 2003/0120185 A1 discloses a massager 10 having a heated applicator pad 28 and a pocket 34 for an enhancement pad 36.

U.S. Pat. No. 9,872,813 B2 shows a messaging head 1 of an appliance A having a massaging finger 21 with a capsule 67 forming a work head 22. A pad 68 may be soaked in a cosmetic product so that the product is dispended by the cap.

U.S. Pat. No. 9,808,646 82 teaches a therapy device 30 having an applicator cartridge 10 with a head 12 and a reservoir 14 delivering for a composition which is photoactive.

U.S. Pat. No. 7,204,846 82 discloses a device 1 having a base portion 19 covered with a cloth 19 and a cotton holder carrying a solution.

U.S. Pat. No. 4,427,001 shows a massager 10 including a main body 11 with a reservoir 19 having a filter opening 20. Dispensing of oil or cream is carried out through openings 22 into a sponge 23 and against rollers 24.

It is therefore seen that many devices have reservoirs containing a product or pads which are soaked in a product. However, the reservoirs are messy and difficult or impossible to clean and they make the device much more complicated and expensive. Pads are messy and hard to keep in place.

Therefore, a need exists to overcome the problems with the prior art as discussed above.

SUMMARY OF THE INVENTION

In accordance with some embodiments, there is provided a capsule to be placed on a head of a device for treating the skin of a user, the capsule includes an inner part, an outer part, and a sidewall that extends from the outer part at an edge of the outer part around an entirely of the outer part, and perpendicular to a surface of the outer part. The capsule further includes a reinforcing ring at a bottom of the sidewall that is sized to retain the capsule on the head of the device, an interior disposed between said inner and outer parts, a product disposed in said interior, and a covering disposed on the surface of said outer part. The covering is removable to allow the product disposed in the interior to be applied to a user's skin.

In accordance with a further feature, the covering is a membrane having a tab that extends outward beyond the sidewall.

In accordance with a further feature, the capsule further included a sterilized package be removed before use.

In accordance with a further feature, the capsule is made of a material that is transparent for a wavelength of light produced by the device, and wherein the material permits light from the device to pass through the capsule and said product disposed therein.

In accordance with a further feature, the surface of the outer part is transparent, matte, or formed into a lens.

In accordance with a further feature, the surface of the outer part is formed as a Fresnel or micro raster lens surface.

In accordance with a further feature, said product is non-transparent and is provided in the interior in a pattern or shape in which there are portions without any of the product.

In accordance with a further feature, the product is a composition having a melting point of 40 degrees C.

In accordance with a further feature, chemical properties, color and viscosity of said product are modified in a predefined manner as a result of application of heat from the device.

In accordance with a further feature, said covering includes indicia thereon.

In accordance with a further feature, further comprises an optical or magnetic mark allowing identification of the product contained therein.

In accordance with a further feature, the capsule is disposable.

In accordance with a further feature, said product is one of day cream, night cream, lotion cream, or mood cream.

In accordance with a further feature, the head of the device has LEDs emitting light.

In accordance with some embodiments, there is provided a skin treatment assembly including a device for treating the skin of a user that includes a head. The assembly further includes a capsule that mounts on said head of the device. The capsule includes an inner part to be removably attached to said head of said device, an outer part having an outer surface that faces away from the device when the capsule is mounted on the head of the device, and a sidewall that extends from the outer part at an edge of the outer part around an entirely of the outer part and perpendicular to the outer surface of the outer part. The capsule further includes a reinforcing ring at a bottom of the sidewall on the inner part that is sized to retain the capsule on the head of the device, an interior disposed between said inner and outer parts, a product disposed in said interior, and a covering being disposed on said outer part and being removable before use.

In accordance with a further feature, wherein said head of said device has LEDs emitting light.

In accordance with some embodiments, there is provided a method for applying a skin care product to a user's skin including providing a device having a head. The head including a light producing element and a heat producing element. The method further including mounting a capsule on the head of the device. The capsule includes an inner part to be removably attached to said head of said device, an outer part having an outer surface that faces away from the device when the capsule is mounted on the head of the device, and a sidewall that extends from the outer part at an edge of the outer part around an entirely of the outer part, and perpendicular to the outer surface of the outer part. The capsule further includes a reinforcing ring at a bottom of the sidewall on the inner part that is sized to retain the capsule on the head of the device, an interior disposed between said inner and outer parts, a product disposed in said interior, and a covering being disposed on said outer part that is being removable. The method further includes removing the covering from the capsule, placing the head of the device into contact proximity with a user's skin such that the outer surface of the outer part makes contact with the user's skin, and enabling at least one of the light producing element of the heat producing element. The product in the interior of the capsule is applied to the user's skin through the outer surface of the outer part of the capsule.

Although the invention is illustrated and described herein as embodied in a disposable cap or capsule for a skin care device, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing Figures, in which like reference numerals are carried forward. The Figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present invention, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant Figure. Those skilled in the art can understand the specific meanings of the above-mentioned terms in the embodiments of the present invention according to the specific circumstances.

BRIEF DESCRIPTION OF THE DRAWINGS

The accompanying Figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
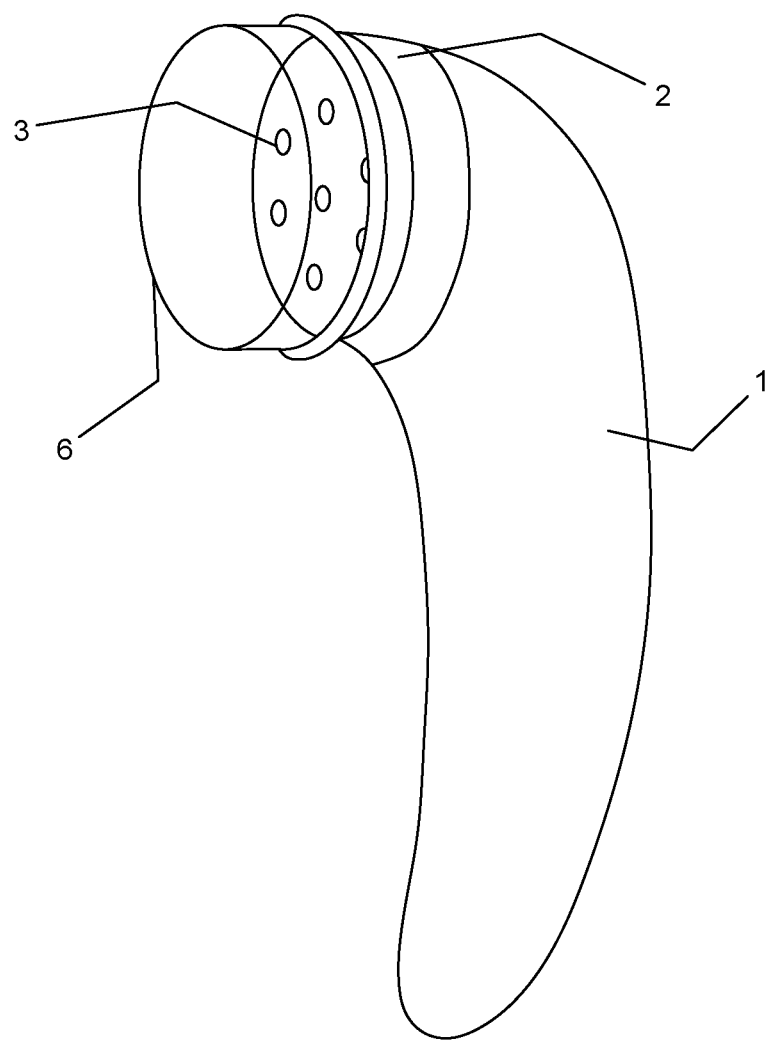
FIG. 1 is a diagrammatic, perspective view of a handheld LED device with the product cap according to the invention.

While the specification concludes with claims defining the features of the invention that are regarded as novel, it is believed that the invention will be better understood from a consideration of the following description in conjunction with the drawing Figures, in which like reference numerals are carried forward. It is to be understood that the disclosed embodiments are merely exemplary of the invention, which can be embodied in various forms.

Referring now to the figures in detail and first, particularly, to FIG. 1 thereof, there is seen a handheld device 1 having a head 2 with LEDs 3 and a product cap or capsule 6 that fits on the head 2 and includes therein a product to be dispensed therefrom during use of the device 1. The device 1 may be the Perfectio by Zero Gravity, which emits red LED light, or a similar device.

Figure 2:
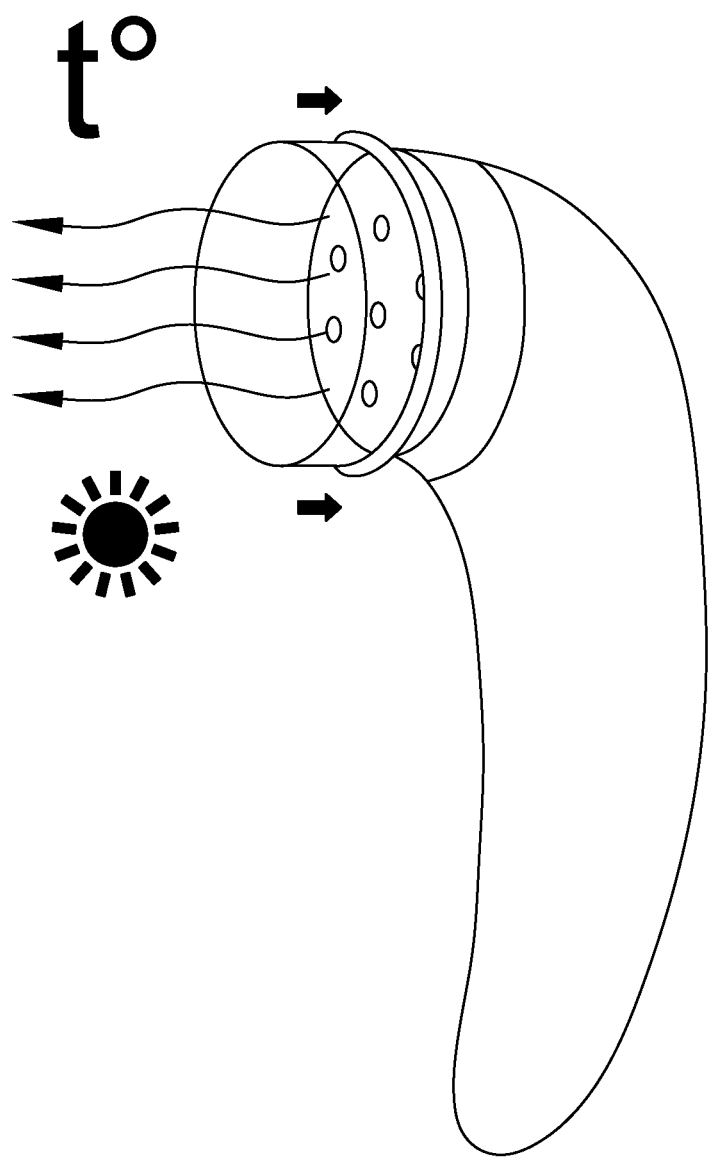
FIG. 2 is a perspective view of the handheld LED device having the product cap and indicating light and heat to be applied to the skin.

The product or cream capsule 6 is made from a material that conducts heat and is transparent along the wavelength of the light emitted by the device 1. It can therefore be seen in FIG. 2 that heat and light from the head 2 of the device 1 pass through the product capsule 6 and the product disposed therein.

Figure 3:
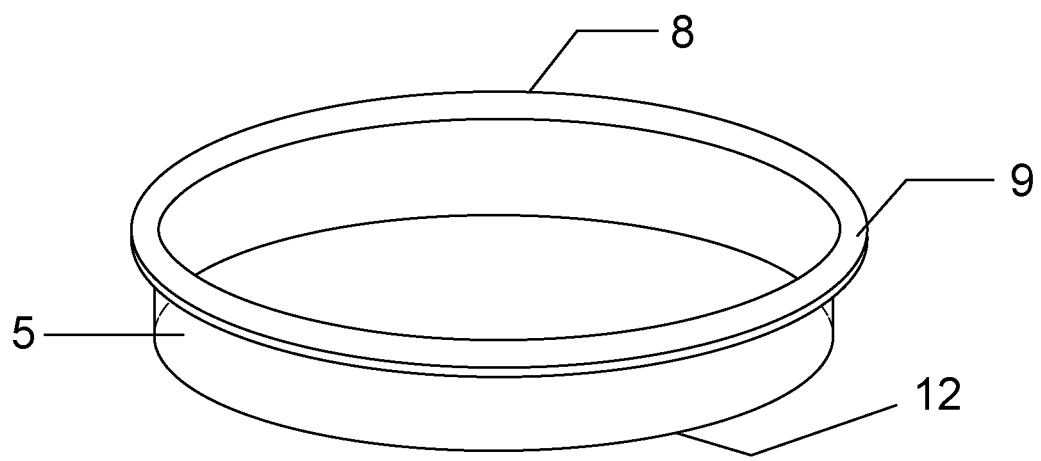
FIG. 3 is a perspective view of an empty product cap.

As is seen in FIG. 3, the product capsule 6 has an inner part 8 that includes a reinforcement ring 9 which allows the product capsule 6 to be attached over the head 2 of the device 1 and keeps the head 2 of the device 1 clean by preventing product inside the product capsule 6 from getting on the face of the head 2. The inner part 8 with the reinforcement ring 9 may be snapped over the head 2 or otherwise held in position, such as by screw threads, a layer of adhesive or a bayonet connection. The reinforcement ring 9 is located at the bottom of a sidewall 5 that extends from the outer part 12 at an edge 18 of the outer part 12 and around an entirety of the outer part 12, and perpendicular to the outer part 12. The outer part 12 faces the user's skin when the product capsule 6 is attached over the head 2 and the device 1 is used on the user's skin.

Figure 4A:
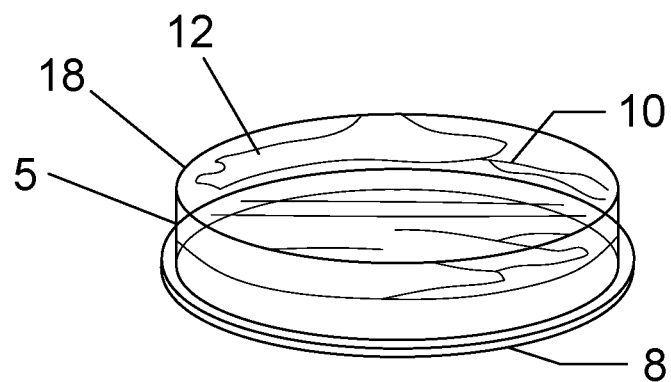
FIGS. 4A, 4B, and 4C are respective perspective, vertical-sectional and perspective views of a product cap filled with a product to be applied to the skin and a sterilized pack for holding the product cap.
Figure 4B:
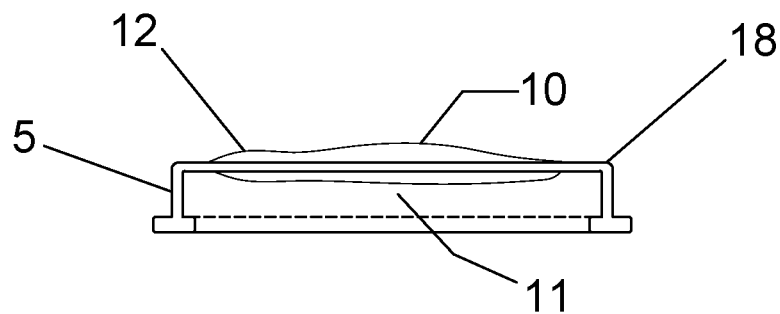

FIGS. 4A and 4B show the product capsule 6 with a layer 10 of a product, such as a cream, oil or lotion, is disposed in an interior 11 of the capsule 6 between the inner part 8 and an outer part 12 facing towards the skin.

Figure 4C:
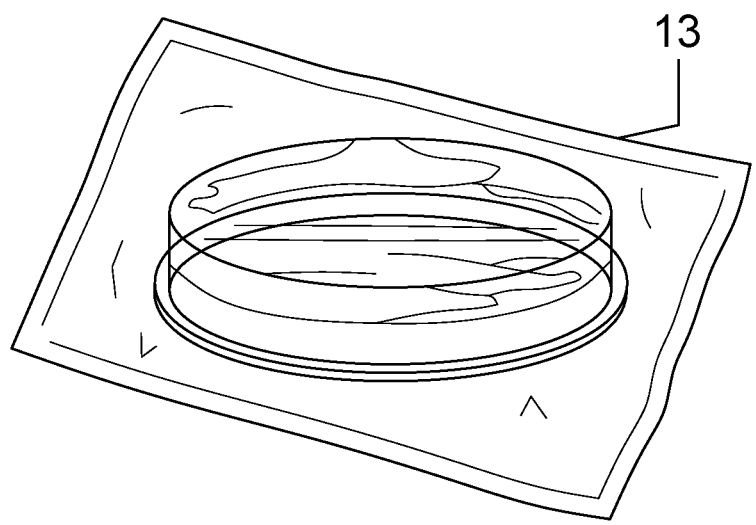

FIG. 4C shows that the capsule 6 containing the product 10 may be held in a covering in the form of a sterilized pack 13 which is shown as being torn open in the figure.

The product or cream can be provided in as a whole layer, in points, in rings, and in any other non-continuous geometrical form which allows penetration of light in the use of non-transparent creams.

The melting point of the cream can be adjusted to the heat of the device in order to achieve a slow release. A slow release is made possible due to a complex of distinct waxes with different melting points. For instance, candelilla wax with a melting point of 60° C.-70° C. and shea butter with a melting point of 35° C. may be used in a ratio of 13:1. As long as the 13:1 wax ratio is maintained, the cream will start to melt at 40° C. so that it never becomes fluid, although the viscosity decreases with increasing temperature.

The chemical properties, color, and viscosity of the cream can be modified in a predefined manner as a result of integration with light and heat waves. Regarding the color, the cream is white, but when melting on the skin it appears transparent. No change is observed in the timeline of the cream (before it is placed on the device and after heating). U.S. Pat. No. 4,996,044 refers to a lipstick formulation and describes a process which is similar to the process employed for the product used in the present invention.

Figure 5A:
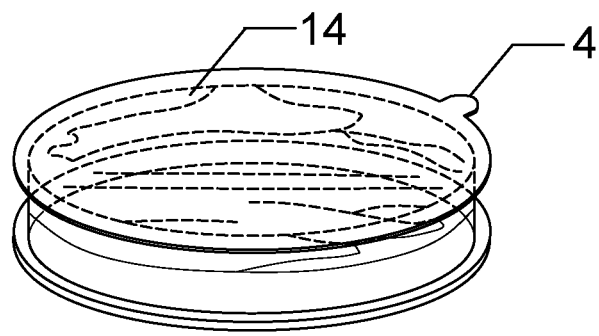
FIGS. 5A and 5B are respective perspective and vertical-sectional views of a product cap filled with a product to be applied to the skin and having a removable membrane.
Figure 5B:
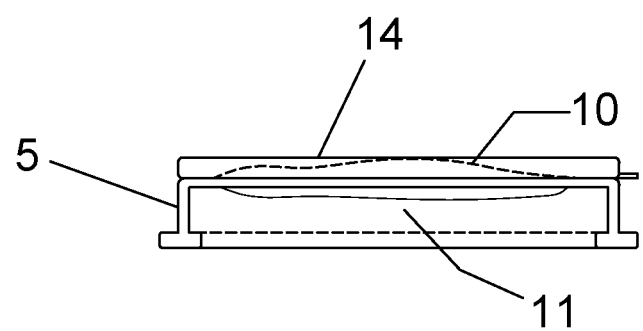

As is seen in FIGS. 5A and 5B, the outer part or top 12 of the capsule 6 has a covering in the form of a membrane 14 that needs be removed before beginning to use the capsule 6. The membrane 14 has a tab 4 that extends outward beyond the sidewall 5 making it easier to remove. The membrane 14 is used as an alternative or in addition to the sterilized pack 13 shown in FIG. 4C as different coverings.

Figure 6A:
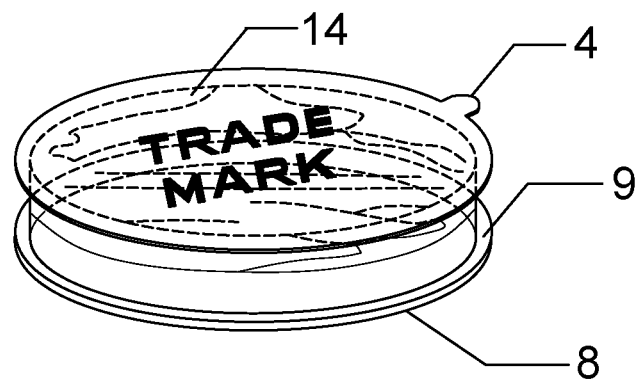
FIGS. 6A and 6B are respective perspective and vertical-sectional views of a product cap filled with a product to be applied to the skin and having a removable membrane with identifying indicia.
Figure 6B:
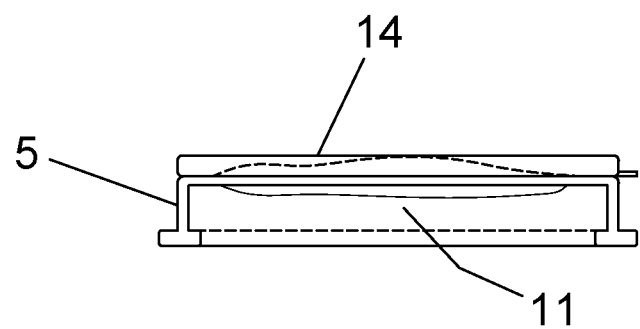

This membrane 14 can include trademark information or any other information, such as an indication of the contents of the capsule 6 or instructions for use, as is shown in FIGS. 6A and 6B.

Figure 7A:
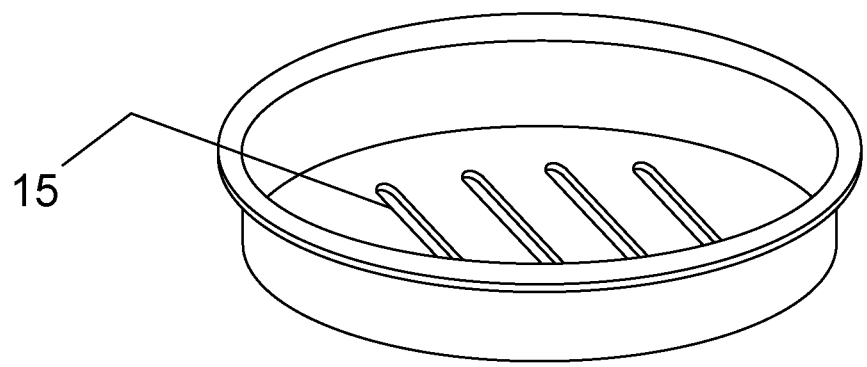
FIGS. 7A and 7B are perspective views of an empty product cap similar to FIG. 3 but respectively having Fresnel and micro raster lenses.
Figure 7B:
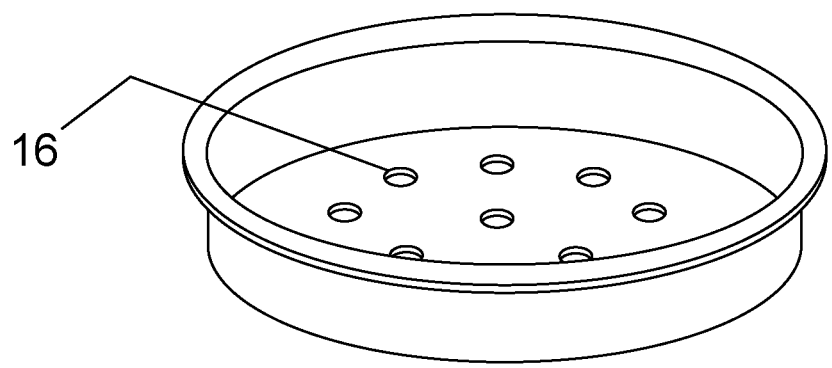

The surface of the capsule 6 may be transparent, matte or with optical properties defined by a different surface such as a Fresnel lens 15 or a micro raster lens 16 to control light scattering and cream adhesion on a surface, as shown in FIGS. 7A and 7B.

Figure 8:
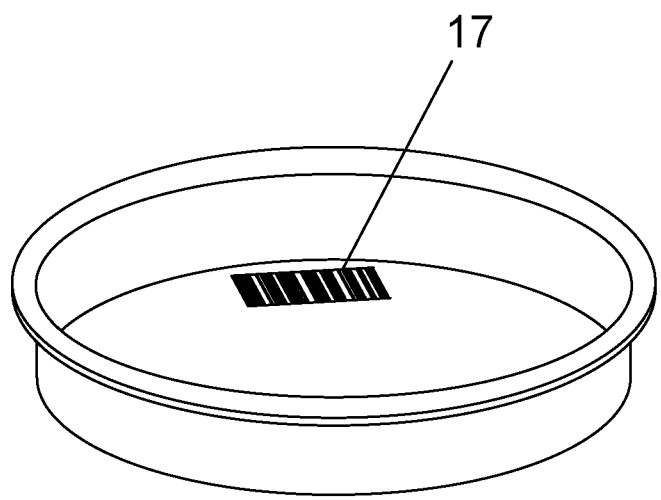
FIG. 8 is a perspective view of an empty product cap similar to FIG. 3 but with an optical or magnetic mark for identification purposes.

FIG. 8 shows that the capsule 6 may have an optical or magnetic mark 17 at any location that allows the identification of the cap and the contents thereof.

The product or cream capsule 6 is disposable. Prior to use, the cream capsule 6 stays in closed packaging 13, 14 and permits easy preservation and selection between different types of products or creams in the caps 6. As an example: day cream, night cream, lotion cream, or mood cream may be provided.

Useful product and marketing information about the cream and its characteristics can be printed on the packaging 13, 14. After removing the capsule 6 from the package 13, 14, the capsule 6 is placed on top of the device 1 and the device or appliance 1 is turned on.

The sterilized pack 13 or the membrane 14 for protecting the product or cream is then removed and after respectively tearing it open or pulling it off, the capsule 6 is ready for use.

Heat and light from the device 1 penetrates through the cap since the capsule 6 is transparent along the wavelength of the device. The heat melts the cream and causes a controlled release. The transparency of the cap allows for an optimum therapeutic effect of the device.

During use, the user moves the device over the skin, gradually rubbing the cream into the skin. The heat of the device in combination with the cream helps to increase the effect of the action.

After using capsule 6, it is removed from the appliance or device 1 and discarded.

A capsule for use with a skin care device is disclosed that allows the capsule to be mounted on the head of the skin care device such that light and heat emitted from the head of the skin care device passes through the capsule into the user's skin. Further, the capsule includes hold a product inside the capsule that can be applied to the user's skin through the outer surface of the capsule. Thus, the capsule provides the benefit of reducing waste of product and reducing, if not eliminating, the need to clean the head of the device.

The claims appended hereto are meant to cover all modifications and changes within the scope and spirit of the present invention.

What is claimed is:

1. A capsule to be placed on a head of a device for treating the skin of a user, the capsule comprising:
    an inner part;
    an outer part;
    a sidewall that extends from the outer part at an edge of the outer part around an entirely of the outer part, and perpendicular to a surface of the outer part;
    a reinforcing ring at a bottom of the sidewall that is sized to retain the capsule on the head of the device;
    an interior disposed between said inner and outer parts;
    a product disposed in said interior; and
    a covering disposed on the surface of said outer part, and wherein the covering is removable to allow the product disposed in the interior to be applied to a user's skin.

2. The capsule according to claim 1, wherein said covering is a membrane having a tab that extends outward beyond the sidewall.

3. The capsule according to claim 1, further including a sterilized package to be removed before use.

4. The capsule according to claim 1, wherein the capsule is made of a material that is transparent for a wavelength of light produced by the device, and wherein the material permits light from the device to pass through the capsule and said product disposed therein.

5. The capsule according to claim 1, wherein the surface of the outer part is transparent, matte, or formed into a lens.

6. The capsule according to claim 5, wherein the surface of the outer part is formed as a Fresnel or micro raster lens surface.

7. The capsule according to claim 1, wherein said product is non-transparent and is provided in the interior in a pattern or shape in which there are portions without any of the product.

8. The capsule according to claim 1, wherein said product is a composition having a melting point of 40 degrees C.

9. The capsule according to claim 1, wherein chemical properties, color and viscosity of said product are modified in a predefined manner as a result of application of heat from the device.

10. The capsule according to claim 1, wherein said covering includes indicia thereon.

11. The capsule according to claim 1, which further comprises an optical or magnetic mark allowing identification of the product contained therein.

12. The capsule according to claim 1, wherein the capsule is disposable.

13. The capsule according to claim 1, wherein said product is one of day cream, night cream, lotion cream, or mood cream.

14. The capsule according to claim 1, wherein the head of the device has LEDs emitting light.

15. A skin treatment assembly, comprising:
    a device for treating the skin of a user, said device having a head; and
    a capsule that mounts on said head of said device, said capsule including:
        an inner part to be removably attached to said head of said device;
        an outer part having an outer surface that faces away from the device when the capsule is mounted on the head of the device;
        a sidewall that extends from the outer part at an edge of the outer part around an entirely of the outer part, and perpendicular to the outer surface of the outer part;
        a reinforcing ring at a bottom of the sidewall on the inner part that is sized to retain the capsule on the head of the device;
        an interior disposed between said inner and outer parts;
        a product disposed in said interior; and
        a covering being disposed on said outer part and being removable before use.

16. The assembly according to claim 15, wherein said head of said device has LEDs emitting light.

17. A method for applying a skin care product to a user's skin, comprising:
    providing a device having a head, the head including a light producing element and a heat producing element;
    mounting a capsule on the head of the device, the capsule having:
        an inner part to be removably attached to said head of said device;
        an outer part having an outer surface that faces away from the device when the capsule is mounted on the head of the device;
        a sidewall that extends from the outer part at an edge of the outer part around an entirely of the outer part, and perpendicular to the outer surface of the outer part;
        a reinforcing ring at a bottom of the sidewall on the inner part that is sized to retain the capsule on the head of the device;
        an interior disposed between said inner and outer parts;
        a product disposed in said interior; and
        a covering being disposed on said outer part that is removable;
    removing the covering from the capsule;
    placing the head of the device into contact proximity with a user's skin such that the outer surface of the outer part makes contact with the user's skin; and
    enabling at least one of the light producing element of the heat producing element;
    wherein the product in the interior of the capsule is applied to the user's skin through the outer surface of the outer part of the capsule.

* * * * *